(12) United States Patent
Nettekoven et al.

(10) Patent No.: US 7,456,174 B2
(45) Date of Patent: Nov. 25, 2008

(54) 5-AMINOINDOLE DERIVATIVES AS H3 INVERSE AGONISTS

(75) Inventors: Matthias Heinrich Nettekoven, Grenzach-Wyhlen (DE); Jean-Marc Plancher, Hagenthal le bas (FR); Olivier Roche, Folgensbourg (FR); Rosa Maria Rodriguez-Sarmiento, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 51 days.

(21) Appl. No.: 11/332,955

(22) Filed: Jan. 17, 2006

(65) Prior Publication Data

US 2006/0160855 A1 Jul. 20, 2006

(30) Foreign Application Priority Data

Jan. 19, 2005 (EP) .................................. 05100312

(51) Int. Cl.
*A61K 31/5377* (2006.01)
*C07D 413/14* (2006.01)

(52) U.S. Cl. .................................... 514/235.2; 544/130

(58) Field of Classification Search ................. 514/323, 514/419, 235.2; 546/201; 548/465; 544/130
See application file for complete search history.

(56) References Cited

U.S. PATENT DOCUMENTS 5,756,507 A * 5/1998 Goulet et al. .......... 514/254.08
2003/0069278 A1 * 4/2003 Zhou et al. ................... 514/338

FOREIGN PATENT DOCUMENTS

| WO | WO 01/74773 | 10/2001 |
| WO | WO 01/74814 | 10/2001 |
| WO | WO 04/000831 | 12/2003 |
| WO | WO 2005/123716 | 12/2005 |

OTHER PUBLICATIONS

Yoshimoto et. al., Proc. Natl. Acad. Sci. USA, Sep. 12, 2006, 103(37), 13866-71.*

Nagai et al., Exp. Biol. Med. (Maywood), Nov. 2003, 228(10) 1138-45.*
Hancock, et al, Expert Opinion Investig. Drugs, Oct. 2004, 13(10), 1237-48.*
Lehmann et al., Drugs, 2003, 63(17), 1785-97.*
Burks 1994 in Johnson L.R. ed., Physiology of the Gastrointestinal Tract, Raven Press, NY, pp. 211-242.
Leurs et al., Br J. Pharmacol. 1991, 102, pp. 179-185.
Raithel et al., Int. Arch. Allergy Immunol. 1995, 108, 127-133.
Panula et al., Proc. Natl. Acad. Sci. USA 1984, 81, 2572-2576.
Inagaki et al., J. Comp. Neurol 1988, 273, 283-300.
Arrang et al., Nature 1983, 302, 832-837.
Arrang et al., Neuroscience 1987, 23, 149-157.
Clapham & Kilpatrick, Br. J. Pharmacol. 1982, 107, 919-923.
Blandina et al. in The Histamine H3 Receptor (Leurs RL and Timmermann H eds, 1998, pp. 27-40, Elsevier, Amsterdam, The Netherlands.
Masaki et al; Endocrinol. 2003, 144, 2741-2748.
Hancock et al., European J. of Pharmacol. 2004, 487, 183-197.
Timmermann, J. Med. Chem. 1990, 33, 4-11.

* cited by examiner

*Primary Examiner*—Bernard Dentz
*Assistant Examiner*—David E Gallis
(74) *Attorney, Agent, or Firm*—George W. Johnston; Dennis P. Tramaloni; Samuel H. Megerditchian

(57) ABSTRACT

The present invention relates to compounds of formula I

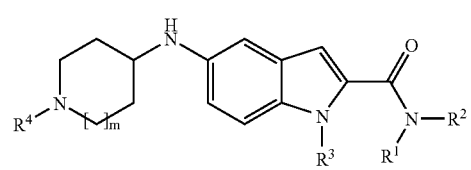

wherein $R^1$, $R^2$, $R^3$, $R^4$ and m are as defined in the description and claims, and pharmaceutically acceptable salts thereof as well as to pharmaceutical compositions comprising these compounds and to methods for their preparation. The compounds are useful for the treatment and/or prevention of diseases which are associated with the modulation of H3 receptors.

11 Claims, No Drawings

5-AMINOINDOLE DERIVATIVES AS H3 INVERSE AGONISTS

PRIORITY TO RELATED APPLICATIONS

This application claims the benefit of European Application No. 05100312.7 filed Jan. 19, 2005, which is hereby incorporated by reference in its entirety.

FIELD OF THE INVENTION

The present invention is directed, for example, to novel indole derivatives, their manufacture, pharmaceutical compositions containing them and their use as medicaments. The active compounds of the present invention are useful in treating obesity and other disorders.

Preferably, the present invention is directed to compounds of the 1 formula:

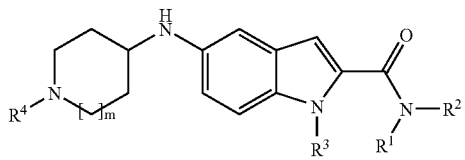

and pharmaceutically acceptable salts thereof.

It has been found that the compounds of formula I are antagonists and/or inverse agonists at the histamine 3 receptor (H3 receptor).

All documents cited or relied upon below are expressly incorporated herein by reference.

BACKGROUND OF THE INVENTION

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the central nervous system (CNS) and the periphery through four distinct histamine receptors, the histamine H1, H2 H3 and H4 receptors.

H3 receptors are predominantly localized in the CNS. As an autoreceptor, H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release.

Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

A need exist, therefore, to provide selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

In one embodiment of the present invention, provided is a compound of the formula I:

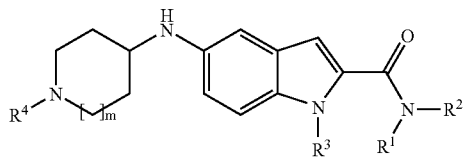

wherein:

$R^1$ and $R^2$ independently from each other are selected from the group consisting of hydrogen, lower alkyl, lower alkenyl, lower alkinyl, cycloalkyl, lower cycloalkylalkyl, lower hydroxyalkyl, lower alkoxyalkyl, lower alkylsulfanylalkyl, lower dialkylaminoalkyl, lower dialkylcarbamoylalkyl, phenyl unsubstituted or substituted with one or two groups independently selected from lower alkyl, lower halogenalkoxy or lower hydroxyalkyl, lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl, and lower heterocyclylalkyl wherein the heterocyclyl ring may be unsubstituted or substituted with one or two lower alkyl groups; or $R^1$ and $R^2$ together with the nitrogen atom to which they are attached form a 4-, 5-, 6- or 7-membered saturated or partly unsaturated heterocyclic ring optionally containing a further heteroatom selected from oxygen or sulfur, said saturated heterocyclic ring being unsubstituted or substituted by one, two or three groups independently selected from lower alkyl, halogen, lower halogenalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy, halogen and lower halogenalkyl;

$R^3$ is hydrogen or lower alkyl;

$R^4$ is selected from the group consisting of lower alkyl, cycloalkyl and lower cycloalkylalkyl;

m is 0, 1 or 2;

and pharmaceutically acceptable salts thereof.

In another embodiment of the present invention, provided is a process for the manufacture of a compound according to formula I, comprising the steps of reacting the compound of the formula II

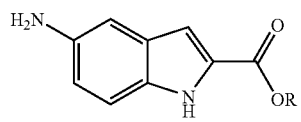

wherein R is lower alkyl, with a ketone of the formula III

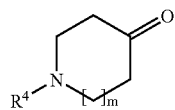

wherein $R^4$ and m are as defined above, in the presence of a reducing agent and an acid to obtain a compound of the formula IV

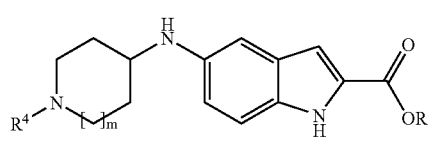

and, after saponification of the ester, coupling the compound of formula V

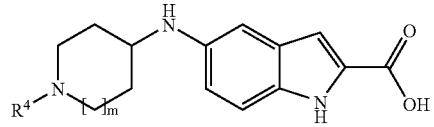

with an amine of the formula VI

$H-NR^1R^2$   VI wherein $R^1$ and $R^2$ are as defined above, under basic conditions to obtain a compound of the formula I

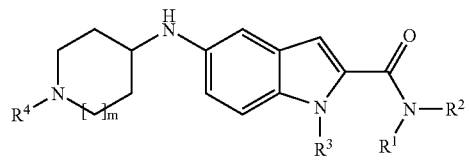

wherein $R^3$ is hydrogen, and optionally alkylating this compound to obtain a compound of formula I, wherein $R^3$ is lower alkyl, and if desired, converting the compound obtained into a pharmaceutically acceptable acid addition salt.

In a further embodiment of the present invention, provided is a pharmaceutical composition, comprising a therapeutically effective amount of a compound according to formula I and a pharmaceutically acceptable carrier and/or adjuvant.

In a yet another embodiment of the present invention, provided is a method for the treatment or prevention of diseases which are associated with the modulation of H3 receptors, comprising the step of administering a therapeutically active amount of a compound according to formula I to a human being or animal in need thereof.

In a still further embodiment of the present invention, provided is a method for the treatment or prevention of obesity in a human being or animal, comprising the step of administering a therapeutically effective amount of a compound of formula I in combination or association with a therapeutically effective amount of other drugs for the treatment of obesity or eating disorders.

In a still another embodiment of the present invention, provided is a method of treatment or prevention of type II diabetes in a human being or animal, comprising the step of administering a therapeutically effective amount of a compound according to formula I in combination or association with a therapeutically effective amount of an anti-diabetic agent.

DETAILED DESCRIPTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "lower alkenyl" or "$C_3$-$C_8$-alkenyl", alone or in combination, signifies a straight-chain or branched alkyl group comprising an olefinic bond and up to 8, preferably up to 6, particularly preferred up to 4 carbon atoms. Examples of alkenyl groups are 1-propenyl, 2-propenyl, isopropenyl, 1-butenyl, 2-butenyl, 3-butenyl and isobutenyl. A preferred example is 2-propenyl.

The term "lower alkinyl" or "$C_3$-$C_8$-alkinyl", alone or in combination, signifies a straight-chain or branched alkyl group comprising a triple bond and up to 8, preferably up to 6, particularly preferred up to 4 carbon atoms. Examples of alkinyl groups include 2-propinyl (propargyl), 1-methyl-2-propinyl, 2-butinyl, 3-butinyl, 2-pentinyl and 1-pentin-3-yl.

The term "cycloalkyl" or "$C_3$-$C_7$-cycloalkyl" means a cycloalkyl ring containing 3 to 7 carbon atoms, such as cyclopropyl, cyclobutyl, cyclopentyl, cyclohexyl or cycloheptyl. The cycloalkyl ring may be substituted as defined herein. Especially preferred is cyclopropyl or cyclopentyl.

The term "lower cycloalkylalkyl" or "$C_3$-$C_7$-cycloalkyl-$C_1$-$C_8$-alkyl" refers to lower alkyl groups as defined above wherein at least one of the hydrogen atoms of the lower alkyl group is replaced by a cycloalkyl group as defined above. Examples of preferred lower cycloalkylalkyl groups are cyclopropylmethyl or cyclopropylmethyl.

The term "lower hydroxyalkyl" or "hydroxy-$C_1$-$C_8$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "alkoxy" refers to the group R'—O—, wherein R' is alkyl. The term "lower alkoxy" refers to the group R'—O—, wherein R' is lower alkyl and the term "lower alkyl" has the previously given significance ("$C_1$-$C_8$-alkoxy"). Examples of lower alkoxy groups are e.g. methoxy, ethoxy, n-propoxy, isopropoxy, n-butoxy, isobutoxy, sec. butoxy and tert.butoxy, preferably methoxy and ethoxy and most preferred methoxy.

The term "lower alkoxyalkyl" or "$C_1$-$C_8$-alkoxy-$C_1$-$C_8$-alkyl." refers to lower alkyl groups as defined above wherein at least one of the hydrogen atoms of the lower alkyl group is replaced by an alkoxy group as defined above. Among the preferred lower alkoxyalkyl groups are methoxymethyl, methoxyethyl and ethoxymethyl, with methoxymethyl being especially preferred.

The term "alkylsulfanyl" or "$C_{1-8}$-alkylsulfanyl" refers to the group R'—S—, wherein R' is lower alkyl and the term "lower alkyl" has the previously given significance. Examples of alkylsulfanyl groups are e.g. methylsulfanyl or ethylsulfanyl.

The term "lower alkylsulfanylalkyl" or "$C_{1-8}$-alkylsulfanyl-$C_{1-8}$-alkyl" refers to lower alkyl groups as defined above wherein at least one of the hydrogen atoms of the lower alkyl groups is replaced by an alkylsulfanyl group, preferably methylsulfanyl. An example for a preferred lower alkylsulfanylalkyl group is 2-methylsulfanylethyl.

The term "halogen" refers to fluorine, chlorine, bromine and iodine, with fluorine, chlorine and bromine being preferred.

The term "lower halogenalkyl" or "halogen-$C_1$-$C_8$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "dialkylamino" refers to the group —NR'R", wherein R' and R" are lower alkyl and the term "lower alkyl" has the previously given significance. A preferred dialkylamino group is dimethylamino. The term "lower dialkylaminoalkyl" or "$C_{1-8}$-dialkylamino-$C_{1-8}$-alkyl" refers to lower alkyl groups as defined above wherein at least one of the hydrogen atoms of the lower alkyl group is replaced by a dialkylamino group, preferably dimethylamino. A preferred lower dialkylaminoalkyl group is 3-dimethylaminopropyl.

The term "carbamoyl" refers to the group —CO—NH$_2$.

The term "dialkylcarbamoyl" or "$C_{1-8}$-dialkylcarbamoyl" refers to the group —CO—NR'R" wherein R' and R" are lower alkyl and the term "lower alkyl" has the previously given significance. A preferred dialkylcarbamoyl group is dimethylcarbamoyl.

The term "lower dialkylcarbamoylalkyl" or "$C_{1-8}$-dialkylcarbamoyl-$C_{1-8}$-alkyl" refers to lower alkyl groups as defined above wherein at least one of the hydrogen atoms of the lower alkyl group is replaced by a dialkylcarbamoyl group as defined herein before. A preferred lower dialkylcarbamoylalkyl groups is dimethylcarbamoylmethyl.

The term "lower phenylalkyl" or "phenyl-$C_{1-8}$-alkyl" refers to lower alkyl groups as defined above wherein at least one of the hydrogen atoms of the lower alkyl group is replaced by a phenyl group. Preferred lower phenylalkyl groups are benzyl or phenethyl.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiamorpholinyl. A preferred heterocyclyl group is piperidinyl.

The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyclyl group as defined above.

The term "form a 4-, 5-, 6- or 7-membered saturated or partly unsaturated heterocyclic ring optionally containing a further heteroatom selected from oxygen or sulfur" refers to a saturated N-heterocyclic ring or a N-heterocyclic ring containing a double bond, which may optionally contain a further oxygen or sulfur atom, such as azetidinyl, pyrrolidinyl, oxazolidinyl, isoxazolidinyl, thiazolidinyl, isothiazolidinyl, piperidinyl, morpholinyl, thiomorpholinyl, or azepanyl. The heterocyclic ring may be unsubstituted or substituted by one, two or three groups independently selected from lower alkyl, halogen, halogenalkyl, hydroxy, lower alkoxy, oxo, phenyl, benzyl, pyridyl and carbamoyl. The heterocyclic ring may also be condensed with a phenyl ring, said phenyl ring being unsubstituted or substituted by one, two or three groups independently selected from lower alkyl, lower alkoxy, halogen and halogenalkyl. An example for such a condensed heterocyclic ring is 3,4-dihydro-1H-isoquinoline.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers.

A carbon atom bonded to four nonidentical substituents is termed a "chiral center".

In detail, the present invention relates to compounds of the general formula

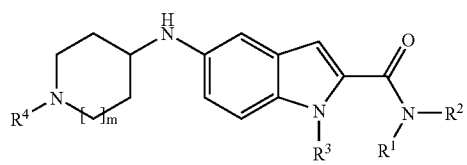

I wherein
R$^1$ and R$^2$ independently from each other are selected from the group consisting of hydrogen, lower alkyl, lower alkenyl, lower alkinyl, cycloalkyl, lower cycloalkylalkyl, lower hydroxyalkyl, lower alkoxyalkyl, lower alkylsulfanylalkyl, lower dialkylaminoalkyl, lower dialkylcarbamoylalkyl, phenyl unsubstituted or substituted with one or two groups independently selected from lower alkyl, lower halogenalkoxy or lower hydroxyalkyl, lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl, and lower heterocyclylalkyl wherein the heterocyclyl ring may be unsubstituted or substituted with one or two lower alkyl groups; or
R$^1$ and R$^2$ together with the nitrogen atom to which they are attached form a 4-, 5-, 6- or 7-membered saturated or partly unsaturated heterocyclic ring optionally containing a further heteroatom selected from oxygen or sulfur,
said saturated heterocyclic ring being unsubstituted or substituted by one, two or three groups independently selected from lower alkyl, halogen, lower halogenalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy, halogen and lower halogenalkyl;
R$^3$ is hydrogen or lower alkyl;
R$^4$ is selected from the group consisting of lower alkyl, cycloalkyl and lower cycloalkylalkyl;
m is 0, 1 or 2;

and pharmaceutically acceptable salts thereof.

Preferred compounds of formula I of the present invention are compounds of formula I, wherein R$^4$ is lower alkyl or cycloalkyl.

Furthermore, compounds of formula I of the present invention are preferred, wherein R$^1$ and R$^2$ together with the nitrogen atom to which they are attached form a 4-, 5-, 6- or 7-membered saturated or partly unsaturated heterocyclic ring optionally containing a further heteroatom selected from oxygen or sulfur, said saturated heterocyclic ring being unsubstituted or substituted by one, two or three groups independently selected from lower alkyl, halogen, lower halogenalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy, halogen and lower halogenalkyl.

Especially preferred are compounds of formula I, wherein R$^1$ and R$^2$ together with the nitrogen atom to which they are attached form a heterocyclic ring selected from the group consisting of morpholine, piperidine, 2,5-dihydropyrrole, pyrrolidine, azepane, azetidine, thiomorpholine and 3,6-dihydro-2H-pyridine,
said heterocyclic ring being unsubstituted or substituted by one, two or three groups independently selected from lower alkyl, halogen, lower halogenalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

Even more preferred are compounds of formula I, wherein R$^1$ and R$^2$ together with the nitrogen atom to which they are attached form a heterocyclic ring selected from the group consisting of morpholinyl, thiomorpholinyl, piperidinyl, 4-methoxypiperidinyl, 4,4-difluoropiperidinyl, 3,3-difluoropiperidinyl, pyrrolidinyl, 2-methylpyrrolidinyl and 3,4-dihydroisoquinolinyl.

Also preferred are compounds of formula I according to the present invention, wherein $R^1$ is selected from the group consisting of hydrogen, lower alkyl, lower alkenyl, lower alkinyl, cycloalkyl, lower cycloalkylalkyl, lower hydroxyalkyl, lower alkoxyalkyl, lower alkylsulfanylalkyl, lower dialkylaminoalkyl, lower dialkylcarbamoylalkyl, phenyl unsubstituted or substituted with one or two groups independently selected from lower alkyl, lower halogenalkoxy or lower hydroxyalkyl, lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl, and lower heterocyclylalkyl wherein the heterocyclyl ring may be unsubstituted or substituted with one or two lower alkyl groups; and $R^2$ is hydrogen or lower alkyl.

Especially preferred are compounds of formula I, wherein $R^1$ and $R^2$ are lower alkyl.

Furthermore, compounds of formula I, wherein $R^3$ is hydrogen, are preferred.

Compounds of formula I according to the present invention, wherein m is 1, thus meaning piperidine groups, are especially preferred.

However, compounds of formula I, wherein m is 0, thus meaning pyrrolidine groups are also preferred.

Further preferred compounds of formula I according to the present invention are those, wherein $R^4$ is lower alkyl.

More preferably, $R^4$ is ethyl or isopropyl.

Compounds of formula I according to the present invention, wherein $R^4$ is cycloalkyl are also preferred. Especially preferred are those compounds of formula I, wherein $R^4$ is cyclopentyl.

Also preferred are compounds of formula I, wherein $R^4$ is lower cycloalkylalkyl, with those compounds being especially preferred, wherein $R^4$ is cycloalkylmethyl, and those compounds, wherein $R^4$ is cyclopropylmethyl, being most preferred.

Examples of preferred compounds of formula I are the following:

[5-(1-ethyl-piperidin-4-ylamino)-1H-indol-2-yl]-morpholin-4-yl-methanone,
[5-(1-ethyl-piperidin-4-ylamino)-1H-indol-2-yl]-piperidin-1-yl-methanone,
[5-(1-isopropyl-piperidin-4-ylamino)-1H-indol-2-yl]-morpholin-4-yl-methanone,
[5-(1-isopropyl-piperidin-4-ylamino)-1H-indol-2-yl]-piperidin-1-yl-methanone,
[5-(1-isopropyl-piperidin-4-ylamino)-1H-indol-2-yl]-pyrrolidin-1-yl-methanone,
[5-(1-isopropyl-piperidin-4-ylamino)-1H-indol-2-yl]-(2-methyl-pyrrolidin-1-yl)-methanone,
[5-(1-isopropyl-piperidin-4-ylamino)-1H-indol-2-yl]-(4-methoxy-piperidin-1-yl)-methanone,
[5-(1-isopropyl-piperidin-4-ylamino)-1H-indol-2-yl]-thiomorpholin-4-yl-methanone,
(3,4-dihydro-1H-isoquinolin-2-yl)-[5-(1-isopropyl-piperidin-4-ylamino)-1H-indol-2-yl]-methanone,
[5-(1-cyclopentyl-piperidin-4-ylamino)-1H-indol-2-yl]-morpholin-4-yl-methanone,
[5-(1-isopropyl-pyrrolidin-3-ylamino)-1H-indol-2-yl]-morpholin-4-yl-methanone bis-hydrochloride,
[5-(1-isopropyl-pyrrolidin-3-ylamino)-1H-indol-2-yl]-piperidine-4-yl-methanone bis-hydrochloride,
[5-(1-isopropyl-pyrrolidin-3-ylamino)-1H-indol-2-yl]-pyrrolidine-4-yl-methanone bis-hydrochloride,
[5-(1-isopropyl-pyrrolidin-3-ylamino)-1H-indol-2-yl]-thiomorpholin-4-yl-methanone bis-hydrochloride,
[5-(1-isopropyl-pyrrolidin-3-ylamino)-1H-indol-2-yl]-4,4-difluoropiperidine-4-yl-methanone bis-hydro chloride,
(3,3-difluoro-piperidin-1-yl)-[5-(1-isopropyl-piperidin-4-ylamino)-1H-indol-2-yl]-methanone,
(4,4-difluoro-piperidin-1-yl)-[5-(1-isopropyl-piperidin-4-ylamino)-1H-indol-2-yl]-methanone,
5-(1-isopropyl-piperidin-4-ylamino)-1H-indole-2-carboxylic acid diethylamide,
5-(1-isopropyl-piperidin-4-ylamino)-1H-indole-2-carboxylic acid isopropyl-methyl-amide,
[5-(1-cyclopropylmethyl-piperidin-4-ylamino)-1H-indol-2-yl]-(4,4-difluoro-piperidin-1-yl)-methanone,
[5-(1-cyclopropylmethyl-piperidin-4-ylamino)-1H-indol-2-yl]-morpholin-4-yl-methanone,
[5-(1-cyclopropyl-piperidin-4-ylamino)-1H-indol-2-yl]-morpholin-4-yl-methanone,
[5-(1-cyclopropyl-piperidin-4-ylamino)-1H-indol-2-yl]-(4,4-difluoro-piperidin-1-yl)-methanone,
[5-(1-tert-butyl-piperidin-4-ylamino)-1H-indol-2-yl]-(4,4-difluoro-piperidin-1-yl)-methanone, and pharmaceutically acceptable salts thereof.

Particularly preferred compounds of formula I of the present invention are the following:

[5-(1-isopropyl-piperidin-4-ylamino)-1H-indol-2-yl]-morpholin-4-yl-methanone,
[5-(1-isopropyl-piperidin-4-ylamino)-1H-indol-2-yl]-piperidin-1-yl-methanone,
[5-(1-isopropyl-piperidin-4-ylamino)-1H-indol-2-yl]-thiomorpholin-4-yl-methanone,
(3,3-difluoro-piperidin-1-yl)-[5-(1-isopropyl-piperidin-4-ylamino)-1H-indol-2-yl]-methanone,
(4,4-difluoro-piperidin-1-yl)-[5-(1-isopropyl-piperidin-4-ylamino)-1H-indol-2-yl]-methanone,
5-(1-isopropyl-piperidin-4-ylamino)-1H-indole-2-carboxylic acid isopropyl-methyl-amide, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartrate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting the compound of the formula II

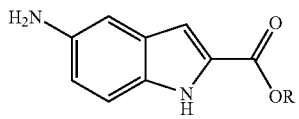

wherein R is lower alkyl, with a ketone of the formula III

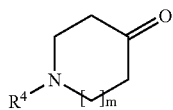

wherein $R^4$ and m are as defined herein before, in the presence of a reducing agent and an acid to obtain a compound of the formula IV

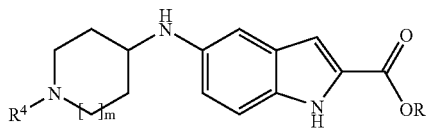

and, after saponification of the ester, coupling the compound of formula V

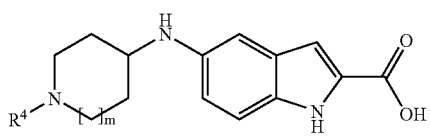

with an amine of the formula VI $$H\!-\!NR^1R^2 \qquad \qquad VI$$

wherein $R^1$ and $R^2$ are as defined herein before, under basic conditions to obtain a compound of the formula I

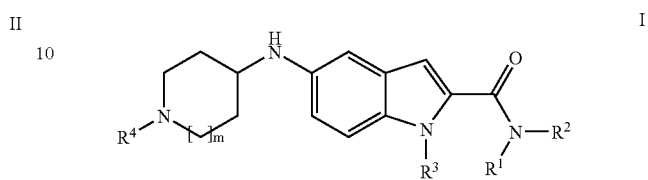

wherein $R^3$ is hydrogen, and optionally alkylating this compound to obtain a compound of formula I, wherein $R^3$ is lower alkyl, and if desired, converting the compound obtained into a pharmaceutically acceptable acid addition salt.

Suitable reducing agents include borane ($BH_3$), sodium boro hydride ($NaBH_4$), sodium cyanoborohydride ($NaBH_3CN$), lithium triethylborohydride (LiH $BEt_3$), sodium triacetoxyborohydride (Na $B(OAc)_3H$), diiosobutylaluminiumhydride (i-$Bu_2AlH$, DIBAH), lithium aluminium hydride ($LiAlH_4$), and the like. Preferred reducing agents are sodium boro hydride or sodium triacetoxy borohydride.

In more detail, the compounds of formula I can be manufactured by the methods given below, by the methods given in the examples or by analogous methods.

The preparation of compounds of formula I of the present invention may be carried out in sequential or convergent synthetic routes. Syntheses of the invention are shown in the following scheme. The skills required for carrying out the reaction and purification of the resulting products are known to those in the art. The substituents and indices used in the following description of the processes have the significance given above unless indicated to the contrary.

Compounds of the general formula I can be prepared according to scheme 1 as follows:

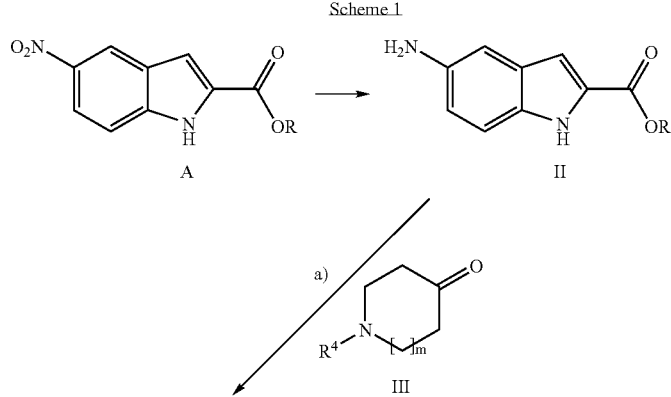

Scheme 1

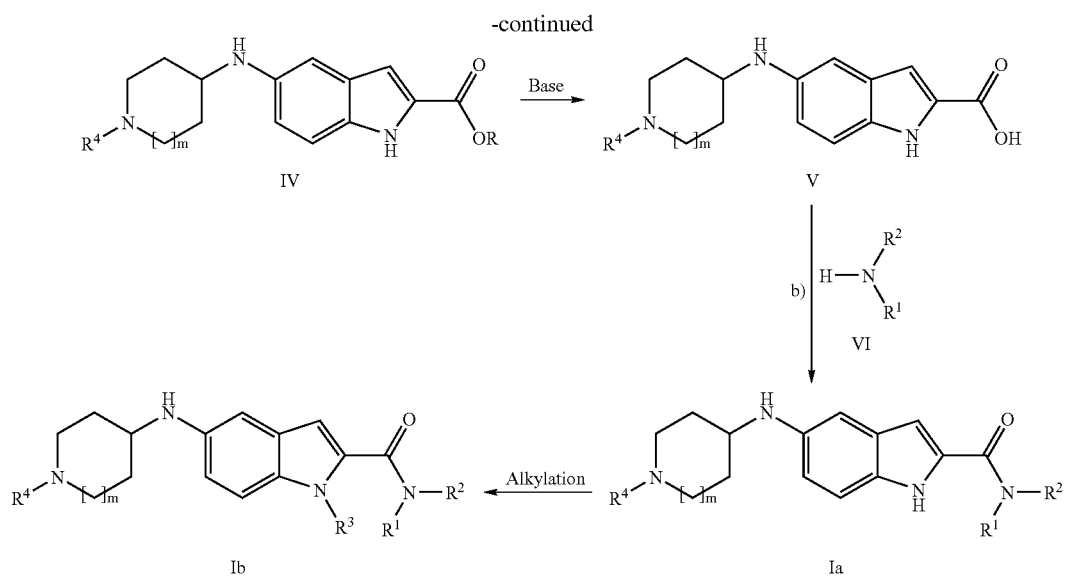

5-Amino-1H-indole-2-carboxylic acid esters II (preferably the ethyl ester) are known in literature and can be synthesized from commercially available starting materials such as 5-nitro-1H-indole-2-carboxylic acid esters A according to the procedures described in literature (Journal of Heterocyclic Chemistry, 26(3), 557-64; 1989; Journal of Medicinal Chemistry, 31(3), 590-603, 1988.). Subsequent modification of the amino functionality can be done according to methods described in literature and the procedures are known to those in the art (For reaction conditions described in literature affecting such reations see for example: Comprehensive Organic Transformations: A Guide to Functional Group Preparations, 2nd Edition, Richard C. Larock. John Wiley & Sons, New York, N.Y. 1999) However, it is convenient to transform the amino functionality in II through reductive animation with a ketone (either commercially available or accessible by methods described in references or by methods known in the art; as appropriate) under reducing conditions. The reaction may be carried out in the presense or absense of a solvent and an acid or Lewis acid. There is no particular restriction on the nature of the solvent to be employed, provided that is has no adverse effect on the reaction or the reagents involved and that it can dissolve the reagents, at least to some extent. Examples for suitable solvents include methanol, THF, and the like. There is no particular restriction on the nature of the acid or Lewis acid used in this stage, and any or Lewis acid commonly used in this type of reaction may equally be employed here. Examples of such acids or Lewis acids include titanium isopropoxide, and the like. There is no particular restriction on the nature of the reducing agent used in this stage, and any reducing agent commonly used in this type of reaction may equally be employed here. Examples of such reducing agent incclude borane ($BH_3$), sodium boro hydride ($NaBH_4$), sodium cyanoborohydride ($NaBH_3CN$), lithium triethylborohydride ($LiH\ BEt_3$), sodium triacetoxyborohydride ($Na\ B(OAc)_3H$), diiosobutylaluminiumhydride (i-$Bu_2AlH$, DIBAH), lithium aluminium hydride ($LiAlH_4$), and the like. However, sodium borohydride or sodium triacetoxyborohydride are preferred. The reaction can take place over a wide range of temperatures, and the precise reaction temperature is not critical in the invention. It is convenient, for example, to carry out the reaction with heating from ambient temperature to reflux. The time required for the reaction may also vary widely, depending on many factors, notably the reaction temperature and the nature of the reagents. However, a period of from 0.5 h to several days will usually suffice to yield indole derivatives IV. In the cases where the reductive amination with the desired functionality does not directly lead to the desired intermediate IV, one might employ N-protected keto-precursors to affect the reaction under the conditions outlined above. Subsequently it will become necessary to manipulate the respective protecting group in a straightforward manner to access the desired functionality on the nitrogen.

The transformation of the ester functionality in IV into the respective amide functionality in I can be affected under various conditions according to methods described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). However, it is convenient to first saponify the ester functionality in IV under basic conditions in the presence or the absence of a solvent to access the intermediate acid of formula V. There is no particular restriction on the nature of the solvent to be employed, provided that it has no adverse effect on the reaction or the reagents involved and that it can dissolve the reagents, at least to some extent. Examples for suitable solvents include methanol, THF, water and the like. There is no particular restriction on the nature of the base used in this stage, and any base commonly used in this type of reaction may equally be employed here. Examples of such bases include lithium hydroxide, sodium hydroxide, and the like. The reaction can take place over a wide range of temperatures, and the precise reaction temperature is not critical to the invention. It is convenient, for example, to carry out the reaction with heating from ambient temperature to reflux. The time required for the reaction may also vary widely, depending on many factors, notably the reaction temperature and the nature of the reagents. However, a period of from 0.5 h to several days will usually suffice to yield the intermediate acid. The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The respective acids of formula V can conveniently be transformed to the respective amide through coupling with an amine of formula VI (either commercially available or accessible by methods described in references or by methods known in the art; as appropriate) by employing the usage of coupling reagents. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo [4,5-b] pyridinium-3-oxide hexafluoro-phosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. It is convenient, for example, to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. It is convenient, for example, to carry out the reaction with heating from ambient temperature to reflux. The time required for the reaction may also vary widely, depending on many factors, notably the reaction temperature and the nature of the reagents. However, a period of from 0.5 h to several days will usually suffice to yield indole derivatives of formula Ia. The indole derivatives of formula Ia can optionally be transformed into the 1-alkyl indole derivatives through a reaction with an alkylating agent such as for example an alkyl iodide and in the presence of a base such as NaH, DIPEA, $Na_2CO_3$ and the like. When carrying out this reaction the 5-amino group might have to be protected with a conventional amino protecting group.

As described above, the compounds of formula I of the present invention can be used as medicaments for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. The use as medicament for the treatment and/or prevention of obesity is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In another embodiment, the invention relates to a method for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. A method for the treatment and/or prevention of obesity is preferred.

The invention further relates to the use of compounds of formula I as defined above for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. The use of compounds of formula I as defined above for the treatment and/or prevention of obesity is preferred.

In addition, the invention relates to the use of compounds of formula I as defined above for the preparation of medicaments for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. The use of compounds of formula I as defined above for the preparation of medicaments for the treatment and/or prevention of obesity is preferred.

It is a further preferred embodiment to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include but are not limited to lipase inhibitors, anorectic agents, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an embodiment of the present invention.

The use of a compound of formula I in the manufacture of a medicament for the treatment and prevention of obesity in a patient who is also receiving treatment with a lipase inhibitor, preferably with tetrahydrolipstatin, is also an embodiment of the present invention.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is orlistat. Also an embodiment of the invention is the method as described above for the simultaneous, separate or sequential administration of a compound according to formula I and a lipase inhibitor, particularly tetrahydrolipstatin.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an embodiment of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an embodiment of the present invention.

It is a further preferred embodiment to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an embodiment of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an embodiment of the present invention.

It is a further preferred embodiment to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan (RO0610612), A308165, and the like.

Also an embodiment of the invention is the method as described above for the simultaneous, separate or sequential administration of a compound according to formula I and a therapeutically effective amount of a anti-hypertensive agent.

The use of a compound of formula I in the manufacture of a medicament for the treatment and prevention of hypertension in a patient who is also receiving treatment with an anti-hypertensive agent, is also an embodiment of the present invention.

The compounds of formula I and their pharmaceutically acceptable salts possess valuable pharmacological properties. Specifically, it has been found that the compounds of the present invention are good histamine 3 receptor (H3R) antagonists and/or inverse agonists.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Intermediate 1

5-Amino-1H-indole-2-carboxylic acid ethyl ester

A solution of 5.1 g (22 mmol) ethyl 5-nitro-2-carboxylate indole in 300 ml THF was hydrogenated over $PtO_2$ with 1 bar $H_2$ for 2 h at room temperature. After filtration and evaporation the residue was purified over silica eluting with a mixture of ethyl acetate/heptane 4/1. After evaporation of the product fractions 4.28 g (96%) of the title compound was yielded as brown solid. MS (m/e): 205.3 ($MH^+$, 100%).

Intermediate 2

5-(1-Ethyl-piperidin-4-ylamino)-1H-indole-2-carboxylic acid ethyl ester

A mixture of 0.204 g (1 mmol) 5-amino-1H-indole-2-carboxylic acid ethyl ester, 133 mg (1 mmol) 1-ethyl piperidone and 0.35 ml (1 mmol) titanium(IV)isopropoxide in 1 ml methanol was treated after 3 h at room temperature with 0.023 g (1 mmol) sodium borohydride and the mixture was allowed to react during 16 h at room temperature. The mixture was poured on 50 ml ice/water and treated with 50 ml ethyl acetate and 5 ml 1 N NaOH aq. After 20 min the mixture was filtered through decalite and the aqueous phase was extracted with 50 ml ethyl acetate. The combined organic phases were washed with 50 ml NaCl sat., dried over $Na_2SO_4$ and after filtration evaporated to dryness. The residue was purified over silica eluting with a gradient of dichloromethane (DCM)/2N $NH_3$ in methanol and 0.240 g (76%) of the title compound were isolated as brown solid. MS (m/e): 316.1 ($MH^+$, 100%).

Intermediate 3

5-(1-Ethyl-piperidin-4-ylamino)-1H-indole-2-carboxylic acid, bis hydrochloride salt A mixture of 0.230 mg (1 mmol) 5-(1-ethyl-piperidin-4-ylamino)-1H-indole-2-carboxylic acid ethyl ester and 31 mg (1 mmol) LiOH.x $H_2O$ in 2 ml THF, 2 ml methanol and 1 ml water was heated to 65° C. for 1 h. After evaporation the mixture was diluted with 5 ml water and 3 ml 1N aq. HCl. The mixture was evaporated to dryness and used without any further purification in the subsequent step. MS (m/e): 288.1 ($MH^+$, 100%).

Intermediate 4

5-(1-Isopropyl-piperidin-4-ylamino)-1H-indole-2-carboxylic acid ethyl ester

According to the procedure described for the synthesis of 5-(1-ethyl-piperidin-4-ylamino)-1H-indole-2-carboxylic acid ethyl ester the title compound was synthesized from 5-amino-1H-indole-2-carboxylic acid ethyl ester and 1-isopropyl piperidone in 69% yield as yellow solid. MS (m/e): 330.5 ($MH^+$, 100%).

Intermediate 5

5-(1-Isopropyl-piperidin-4-ylamino)-1H-indole-2-carboxylic acid

According to the procedure described for the synthesis of 5-(1-ethyl-piperidin-4-ylamino)-1H-indole-2-carboxylic acid the title compound was synthesized from 5-(1-Isopropyl-piperidin-4-ylamino)-1H-indole-2-carboxylic acid ethyl ester by treatment with LiOH.$H_2O$. The product was used without further purification in the subsequent step. (m/e): 302.0 ($MH^+$, 100%).

Intermediate 6

5-(1-Cyclopentyl-piperidin-4-ylamino)-1H-indole-2-carboxylic acid ethyl ester

According to the procedure described for the synthesis of 5-(1-ethyl-piperidin-4-ylamino)-1H-indole-2-carboxylic acid ethyl ester the title compound was synthesized from 5-Amino-1H-indole-2-carboxylic acid ethyl ester and 1-cyclopentyl piperidone in 67% yield as brown solid. MS (m/e): 356.3 ($MH^+$, 100%).

Intermediate 7

5-(1-Cyclopentyl-piperidin-4-ylamino)-1H-indole-2-carboxylic acid

According to the procedure described for the synthesis of 5-(1-ethyl-piperidin-4-ylamino)-1H-indole-2-carboxylic acid the title compound was synthesized from 5-(1-cyclopentyl-piperidin-4-ylamino)-1H-indole-2-carboxylic acid ethyl ester by treatment with LiOH x.$H_2O$. The product was used without further purification and characterization in the subsequent step.

Intermediate 8

5-(1-Benzyl-pyrrolidin-3-ylamino)-1H-indole-2-carboxylic acid ethyl ester

According to the procedure described for the synthesis of 5-(1-ethyl-piperidin-4-ylamino)-1H-indole-2-carboxylic acid ethyl ester the title compound was synthesized from 5-amino-1H-indole-2-carboxylic acid ethyl ester and 1-benzyl pyrrolidin-3-one in 39% yield as light brown foam. MS (m/e): 364.3 (MH$^+$, 100%).

Intermediate 9

5-(Pyrrolidin-3-ylamino)-1H-indole-2-carboxylic acid ethyl ester

A solution of 2.8 g (7 mmol) 5-(1-benzyl-pyrrolidin-3-ylamino)-1H-indole-2-carboxylic acid ethyl ester in 180 ml ethanol and 20 ml acetic acid was hydrogenated over Pd/C for 24 h at room temperature. After filtration and evaporation the residue was taken up in 200 ml 10% NaHCO$_3$ aq. and extracted with 150 ml dichloromethane (DCM). The aqueous phase was washed 7 times with 80 ml DCM each and the combined organic phases were dried over Na$_2$SO$_4$. After filtration and evaporation to dryness the residue was purified over Isolute® SPE (solid phase extraction) eluting with a gradient formed from DCM/2N NH$_3$ in methanol to yield 1.05 g (74%) of the title compound and light brown crystals. MS (m/e): 274.3 (MH$^+$, 100%).

Intermediate 10

5-(1-Isopropyl-pyrrolidin-3-ylamino)-1H-indole-2-carboxylic acid ethyl ester A mixture of 0.2 g (1 mmol) 5-(pyrrolidin-3-ylamino)-1H-indole-2-carboxylic acid ethyl ester, 0.042 g (1 mmol) acetone and 0.1 ml acetic acid in 10 ml THF was treated after 1 h with 0.233 g (1 mmol) sodium trisacetoxyborohydride at 0° C. The mixture was allowed to react for 39 h at room temperature. The mixture was treated with 5 ml water, 15 ml Na$_2$CO$_3$ aq. and 15 ml ethyl acetate and the aqueous phase was extracted with 40 ml ethyl acetate. The combined organic phases were dried over Na$_2$SO4, filtered and evaporated to dryness. The residue was purified over silica eluting with a gradient formed from DCM/2N NH$_3$ in methanol to yield 0.17 g (74%) of the title compound and light brown solid. MS (m/e): 316.3 (MH$^+$, 100%).

Intermediate 11

5-(1-Isopropyl-pyrrolidin-3-ylamino)-1H-indole-2-carboxylic acid

According to the procedure described for the synthesis of 5-(1-ethyl-piperidin-4-ylamino)-1H-indole-2-carboxylic acid the title compound was synthesized from 5-(1-isopropyl-pyrrolidin-3-ylamino)-1H-indole-2-carboxylic acid ethyl ester by treatment with LiOH x.H$_2$O. The product was used without further purification in the subsequent step. MS (m/e): 288.0 (MH$^+$, 100%).

Intermediate 12

5-(1-Cyclopropylmethyl-piperidin-4-ylamino)-1H-indole-2-carboxylic acid, bis hydrochloride salt Step 1: 1-Cyclopropylmethyl-piperidin-4-one To a suspension of bromomethyl cyclopropane (4 mmol) and 4-piperidone hydrate hydrochloride (4 mmol) in acetonitrile (30 mL) was added sodium carbonate (11 mmol). The reaction mixture was stirred 16 h at 85° C. The resulting suspension was filtered and the solid was washed with acetonitrile. The filtrate was concentrated in vacuo and purified by column chromatography on silica eluting with DCM/2N NH$_3$ in methanol 97:3 to yield 339 mg of the title compound as yellow oil. MS (m/e): 154.2 (MH$^+$, 100%).

Step 2: 5-(1-Cyclopropylmethyl-piperidin-4-ylamino)-1H-indole-2-carboxylic acid ethyl ester According to the procedure described for the synthesis of 5-(1-ethyl-piperidin-4-ylamino)-1H-indole-2-carboxylic acid ethyl ester (Intermediate 2) the title compound was synthesized from 5-amino-1H-indole-2-carboxylic acid ethyl ester (Intermediate 1) and 1-cyclopropylmethyl-piperidin-4-one.

MS (m/e): 342.5 (MH$^+$, 100%)

Step 3: 5-(1-Cyclopropylmethyl-piperidin-4-ylamino)-1H-indole-2-carboxylic acid, bis hydrochloride salt According to the procedure described for the synthesis of 5-(1-ethyl-piperidin-4-ylamino)-1H-indole-2-carboxylic acid, bis hydrochloride salt (Intermediate 3) the title compound was synthesized from 5-amino-1H-indole-2-carboxylic acid ethyl ester (Intermediate 1) and 1-cyclopropylmethyl-piperidin-4-one.

MS (m/e): 314.5 (MH$^+$, 100%)

Intermediate 13

5-(1-Cyclopropyl-piperidin-4-ylamino)-1H-indole-2-carboxylic acid, bis hydrochloric salt Step 1: 3-[Cyclopropyl-(2-ethoxycarbonyl-ethyl)-amino]-propionic acid ethyl ester A mixture of ethyl acrylate (300 mmol) and cyclopropyl amine (149 mmol) in absolute ethanol (45 mL) was stirred for 24 h at room temperature. The crude mixture was purified by fractionated distillation in vacuo (20 mbar). One fraction was collected (boiling point: 135° C. at 20 mbar), yielding to 20.58 g of the desired product as a colorless oil. MS (m/e): 274.3 (MH$^+$, 100%).

Step 2: 1-Cyclopropyl-piperidin-4-one

A solution of 3-[cyclopropyl-(2-ethoxycarbonyl-ethyl)-amino]-propionic acid ethyl ester (39 mmol) in anhydrous tetrahydrofuran (65 mL) was added dropwise to a solution of sodium hydride (60% oil dispersion, 58 mmol) in anhydrous tetrahydrofuran (65 mL). Absolute ethanol (39 mmol) was then added. The resulting mixture was heated under reflux for 24 h. The solution obtained was neutralized (pH: 7) with diluted acetic acid and partitioned between water and ethyl acetate. The aqueous layer was extracted with ethyl acetate. The combined extracts were dried over sodium sulfate and the solvent was removed in vacuo, yielding to 10.2 g of reddish oil.

This crude oil was then heated under reflux in 18% w/w hydrochloric acid (130 mL) for 5 h. After basification with sodium hydroxide (ca. 31 g, pH: ca. 12), the crude mixture was extracted with ethyl acetate. The combined extracts were dried over sodium sulfate and the solvent was removed in vacuo. The crude mixture was purified by fractionated distillation in vacuo (20 mbar). One fraction was collected (boiling point: 75° C. at 20 mbar), yielding to 3.6 g (67%) of the desired product as a colorless oil. MS (m/e): 140.0 (MH$^+$, 100%).

Step 3: 5-(1-Cyclopropyl-piperidin-4-ylamino)-1H-indole-2-carboxylic acid ethyl ester According to the procedure described for the synthesis of 5-(1-ethyl-piperidin-4-ylamino)-1H-indole-2-carboxylic acid ethyl ester (Intermediate 2) the title compound was synthesized from 5-amino-1H-indole-2-carboxylic acid ethyl ester (Intermediate 1) and 1-cyclopropyl-piperidin-4-one.

Yellow solid. MS (m/e): 328.5 (MH$^+$, 100%).

Step 4: 5-(1-Cyclopropyl-piperidin-4-ylamino)-1H-indole-2-carboxylic acid, bis hydrochloric salt According to the procedure described for the synthesis of 5-(1-ethyl-piperidin-4-ylamino)-1H-indole-2-carboxylic acid, bis hydrochloride salt (Intermediate 3) the title compound was synthesized from 5-(1-cyclopropyl-piperidin-4-ylamino)-1H-indole-2-carboxylic acid ethyl ester.

Brown solid. MS (m/e): 300.4 (MH$^+$, 100%).

Intermediate 14

5-(1-tert-butyl-piperidin-4-ylamino)-1H-indole-2-carboxylic acid, bis hydrochloric salt Step 1: 3-[tert-Butyl-(2-ethoxycarbonyl-ethyl)-amino]-propionic acid ethyl ester A mixture of ethyl acrylate (0.735 mol) and tert-butyl amine (0.210 mol) was refluxed for 6 days. The crude mixture was purified by fractionated distillation in vacuo (5 mbar). One fraction was collected (boiling point: 120° C. at 5 mbar), yielding to 8.3 g of the desired product as a light yellow oil. MS (m/e): 274.4 (MH$^+$, 100%).

Step 2: 1-tert-Butyl-piperidin-4-one

According to the procedure described for the synthesis of 1-cyclopropyl-piperidin-4-one (Intermediate 13, step 2) the title compound was synthesized from 3-[tert-butyl-(2-ethoxycarbonyl-ethyl)-amino]-propionic acid ethyl ester.

Yellow solid. MS (m/e): 156.2 (MH$^+$, 100%).

Step 3: 5-(1-tert-butyl-piperidin-4-ylamino)-1H-indole-2-carboxylic acid ethyl ester According to the procedure described for the synthesis of 5-(1-ethyl-piperidin-4-ylamino)-1H-indole-2-carboxylic acid ethyl ester (Intermediate 2) the title compound was synthesized from 5-amino-1H-indole-2-carboxylic acid ethyl ester (Intermediate 1) and 1-tert-butyl-piperidin-4-one.

Brown solid. MS (m/e): 344.5 (MH$^+$, 100%).

Step 4: 5-(1-tert-butyl-piperidin-4-ylamino)-1H-indole-2-carboxylic acid, bis hydrochloric salt According to the procedure described for the synthesis of 5-(1-ethyl-piperidin-4-ylamino)-1H-indole-2-carboxylic acid, bis hydrochloride salt (Intermediate 3) the title compound was synthesized from 5-(1-tert-butyl-piperidin-4-ylamino)-1H-indole-2-carboxylic acid ethyl ester.

Brown solid. MS (m/e): 316.4 (MH$^+$, 100%).

Example 1

[5-(1-Ethyl-piperidin-4-ylamino)-1H-indol-2-yl]-morpholin-4-yl-methanone

A mixture of 0.15 g 5-(1-ethyl-piperidin-4-ylamino)-1H-indole-2-carboxylic acid (intermediate 3), 0.16 g O-benzotriazol-1-yl-N,N,N',N'-tetramethyluronium tetrafluoroborate (TBTU), 0.323 g DIPEA and 0.044 g morpholine in 2 ml DMF was reacted for 1 h at room temperature and evaporated to dryness. The residue was treated with ethyl acetate, water and NaHCO$_3$ aq. The aqueous phases were further extracted with ethyl acetate and the combined organic phases were dried over Na$_2$SO$_4$, filtered and evaporated. The residue was further purified by chromatography and crystallization to yield 0.09 g (60%) of the title compound as light brown solid. MS (m/e): 357.4 (MH$^+$, 100%).

According to the procedure described for the synthesis of [5-(1-ethyl-piperidin-4-ylamino)-1H-indol-2-yl]-morpholin-4-yl-methanone further indole derivatives were synthesized from the respective acid intermediates and commercially available amines. For some of the examples the purification procedure was adapted and chosen according to the nature of the product. However, the final products were either chromatographed, re-crystallised (with or without the addition of acid in order to form the respective salt) or both. The respective starting materials as well as the results are shown in table 1 and comprise Example 2 to Example 19.

TABLE 1

| No | MW | Name | Starting materials | MH$^+$ found |
|---|---|---|---|---|
| 2 | 354.49 | [5-(1-ethyl-piperidin-4-ylamino)-1H-indol-2-yl]-piperidin-1-yl-methanone | 5-(1-ethyl-piperidin-4-ylamino)-1H-indole-2-carboxylic acid, bis hydrochloride salt (intermediate 3) and piperidine | 355.5 |
| 3 | 370.49 | [5-(1-isopropyl-piperidin-4-ylamino)-1H-indol-2-yl]-morpholin-4-yl-methanone | 5-(1-isopropyl-piperidin-4-ylamino)-1H-indole-2-carboxylic acid (intermediate 5) and morpholine | 371.3 |
| 4 | 368.52 | [5-(1-isopropyl-piperidin-4-ylamino)-1H-indol-2-yl]-piperidin-1-yl-methanone | 5-(1-isopropyl-piperidin-4-ylamino)-1H-indole-2-carboxylic acid (intermediate 5) and piperidine | 369.3 |
| 5 | 354.49 | [5-(1-isopropyl-piperidin-4-ylamino)-1H-indol-2-yl]-pyrrolidin-1-yl-methanone | 5-(1-isopropyl-piperidin-4-ylamino)-1H-indole-2-carboxylic acid (intermediate 5) and pyrrolidine | 355.4 |
| 6 | 368.52 | [5-(1-isopropyl-piperidin-4-ylamino)-1H-indol-2-yl]-(2-methyl-pyrrolidin-1-yl)-methanone | 5-(1-isopropyl-piperidin-4-ylamino)-1H-indole-2-carboxylic acid (intermediate 5) and 2-methyl-pyrrolidine | 369.3 |
| 7 | 398.55 | [5-(1-isopropyl-piperidin-4-ylamino)-1H-indol-2-yl]-(4-methoxy-piperidin-1-yl)-methanone | 5-(1-isopropyl-piperidin-4-ylamino)-1H-indole-2-carboxylic acid (intermediate 5) and 4-methoxy-piperidine | 399.5 |
| 8 | 386.56 | [5-(1-isopropyl-piperidin-4-ylamino)-1H-indol-2-yl]-thiomorpholin-4-yl-methanone | 5-(1-isopropyl-piperidin-4-ylamino)-1H-indole-2-carboxylic acid (intermediate 5) and thiomorpholine | 387.5 |
| 9 | 416.57 | (3,4-dihydro-1H-isoquinolin-2-yl)-[5-(1-isopropyl-piperidin-4-ylamino)-1H-indol-2-yl]-methanone | 5-(1-isopropyl-piperidin-4-ylamino)-1H-indole-2-carboxylic acid (intermediate 5) and 1,2,3,4-tetrahydro-isoquinoline | 417.4 |

TABLE 1-continued

| No | MW | Name | Starting materials | MH+ found |
|---|---|---|---|---|
| 10 | 396.53 | [5-(1-cyclopentyl-piperidin-4-ylamino)-1H-indol-2-yl]-morpholin-4-yl-methanone | 5-(1-cyclopentyl-piperidin-4-ylamino)-1H-indole-2-carboxylic acid (intermediate 7) and morpholine | 397.3 |
| 11 | 429.39 | [5-(1-isopropyl-pyrrolidin-3-ylamino)-1H-indol-2-yl]-morpholin-4-yl-methanone bis-hydrochloride | 5-(1-isopropyl-pyrrolidin-3-ylamino)-1H-indole-2-carboxylic acid (intermediate 11) and morpholine | 357.4 |
| 12 | 427.42 | [5-(1-isopropyl-pyrrolidin-3-ylamino)-1H-indol-2-yl]-piperidine-4-yl-methanone bis-hydrochloride | 5-(1-isopropyl-pyrrolidin-3-ylamino)-1H-indole-2-carboxylic acid (intermediate 11) and piperidine | 355.5 |
| 13 | 413.39 | [5-(1-isopropyl-pyrrolidin-3-ylamino)-1H-indol-2-yl]-pyrrolidine-4-yl-methanone bis-hydrochloride | 5-(1-isopropyl-pyrrolidin-3-ylamino)-1H-indole-2-carboxylic acid (intermediate 11) and pyrrolidine | 341.4 |
| 14 | 445.46 | [5-(1-isopropyl-pyrrolidin-3-ylamino)-1H-indol-2-yl]-thiomorpholin-4-yl-methanone bis-hydrochloride | 5-(1-isopropyl-pyrrolidin-3-ylamino)-1H-indole-2-carboxylic acid (intermediate 11) and thiomorpholine | 373.3 |
| 15 | 463.4 | [5-(1-isopropyl-pyrrolidin-3-ylamino)-1H-indol-2-yl]-4,4-difluoropiperidine-4-yl-methanone bis-hydrochloride | 5-(1-isopropyl-pyrrolidin-3-ylamino)-1H-indole-2-carboxylic acid (intermediate 11) and 4,4-difluoropiperidine | 391.4 |
| 16 | 404.5 | (3,3-difluoro-piperidin-1-yl)-[5-(1-isopropyl-piperidin-4-ylamino)-1H-indol-2-yl]-methanone | 5-(1-isopropyl-piperidin-4-ylamino)-1H-indole-2-carboxylic acid (intermediate 5) and 3,3-difluoropiperidine | 405.5 |
| 17 | 404.5 | (4,4-difluoro-piperidin-1-yl)-[5-(1-isopropyl-piperidin-4-ylamino)-1H-indol-2-yl]-methanone | 5-(1-isopropyl-piperidin-4-ylamino)-1H-indole-2-carboxylic acid (intermediate 5) and 4,4-difluoropiperidine | 405.5 |
| 18 | 356.51 | 5-(1-isopropyl-piperidin-4-ylamino)-1H-indole-2-carboxylic acid diethylamide | 5-(1-isopropyl-piperidin-4-ylamino)-1H-indole-2-carboxylic acid (intermediate 5) and N,N-diethylamine | 357.1 |
| 19 | 356.51 | 5-(1-isopropyl-piperidin-4-yloxy)-1H-indole-2-carboxylic acid isopropyl-methyl-amide | 5-(1-isopropyl-piperidin-4-ylamino)-1H-indole-2-carboxylic acid (intermediate 5) and isopropyl-methyl-amine | 357.1 |
| 20 | 416.51 | [5-(1-cyclopropylmethyl-piperidin-4-ylamino)-1H-indol-2-yl]-(4,4-difluoro-piperidin-1-yl)-methanone | 5-(1-cyclopropylmethyl-piperidin-4-ylamino)-1H-indole-2-carboxylic acid, bis hydrochloride salt (intermediate 12) and 4,4-difluoropiperidine | 417.5 |
| 21 | 382.51 | [5-(1-cyclopropylmethyl-piperidin-4-ylamino)-1H-indol-2-yl]-morpholin-4-yl-methanone | 5-(1-cyclopropylmethyl-piperidin-4-ylamino)-1H-indole-2-carboxylic acid, bis hydrochloride salt (intermediate 12) and morpholine | 383.5 |
| 22 | 368.48 | [5-(1-cyclopropyl-piperidin-4-ylamino)-1H-indol-2-yl]-morpholin-4-yl-methanone | 5-(1-cyclopropyl-piperidin-4-ylamino)-1H-indole-2-carboxylic acid, bis hydrochloric salt (intermediate 13) and morpholine | 369.5 |
| 23 | 402.49 | [5-(1-cyclopropyl-piperidin-4-ylamino)-1H-indol-2-yl]-(4,4-difluoro-piperidin-1-yl)-methanone | 5-(1-cyclopropyl-piperidin-4-ylamino)-1H-indole-2-carboxylic acid, bis hydrochloric salt (intermediate 13) and 4,4-difluoropiperidine | 403.5 |
| 24 | 418.53 | [5-(1-tert-butyl-piperidin-4-ylamino)-1H-indol-2-yl]-(4,4-difluoro-piperidin-1-yl)-methanone | 5-(1-tert-butyl-piperidin-4-ylamino)-1H-indole-2-carboxylic acid, bis hydrochloric salt (intermediate 14) and 4,4-difluoropiperidine | 419.5 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 26

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 27

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example 28

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 29

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Example 30

The following test was carried out in order to determine the activity of the compounds of formula (I).

Binding Assay with $^3$H-(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R)α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard top-counter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 μM to 0.3 nM) of the selected compounds were always tested in competition binding experiments using membrane of the human HR3—CHO cell line. An appropriate amount of protein, e.g. approximately 500 cpm binding of RAMH at Kd, were incubated for 1 hour at room temperature in 250 μl final volume in 96-well plates in presence of $^3$H(R)α-Methylhistamine (1 nM final concentration=Kd). Non-specific binding was determined using a 200 fold excess of cold (R)α-Methylhistamine dihydrobromide.

All compounds were tested at a single concentration in duplicates. Compounds that showed an inhibition of [$^3$H]-RAMH by more than 50% were tested again to determine $IC_{50}$ in a serial dilution experiment. Ki's were calculated from $IC_{50}$ based on Cheng-Prusoff equation (Cheng, Y, Prusoff, W H (1973) Biochem Pharmacol 22, 3099-3108).

The compounds of the present invention exhibit $K_i$ values within the range of about 1 nM to about 1000 nM, preferably of about 1 nM to about 300 nM, and more preferably of about 1 nM to about 100 nM. The following table shows measured values for some selected compounds of the present invention.

The following table shows measured values for some selected compounds of the present invention.

| | $K_i$ (nM) |
|---|---|
| Example 3 | 47.5 |
| Example 11 | 256 |
| Example 19 | 66 |

It is to be understood that the invention is not limited to the particular embodiments of the invention described above, as variations of the particular embodiments may be made and still fall within the scope of the appended claims.

The invention claimed is:

1. A compound of the formula I:

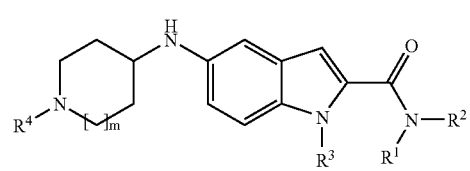

wherein:
   $R^1$ and $R^2$ together with the nitrogen atom to which they are attached form a saturated morpholinyl heterocyclic ring, said saturated heterocyclic ring being unsubstituted or substituted by one, two or three groups independently selected from lower alkyl, halogen, lower halogenalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy, halogen and lower halogenalkyl;
   $R^3$ is hydrogen;

$R^4$ is selected from the group consisting of lower alkyl, cycloalkyl and lower cycloalkylalkyl;
m is 1;
and pharmaceutically acceptable salts thereof.

2. The compound according to claim 1, wherein $R^4$ is lower alkyl or cycloalkyl.

3. The compound according to claim 1, wherein $R^4$ is lower alkyl.

4. The compound according to claim 1, wherein $R^4$ is ethyl or isopropyl.

5. The compound according to claim 1, wherein $R^4$ is cycloalkyl.

6. The compound according to claim 1, wherein $R^4$ is lower cycloalkylalkyl.

7. The compound according to claim 1, selected from the group consisting of
[5-(1-ethyl-piperidin-4-ylamino)-1H-indol-2-yl]-morpholin-4-yl-methanone,
[5-(1-isopropyl-piperidin-4-ylamino)-1H-indol-2-yl]-morpholin-4-yl-methanone,
[5-(1-cyclopentyl-piperidin-4-ylamino)-1H-indol-2-yl]-morpholin-4-yl-methanone,
[5-(1-cyclopropylmethyl-piperidin-4-ylamino)-1H-indol-2-yl]-morpholin-4-yl-methanone,
[5-(1-cyclopropyl-piperidin-4-ylamino)-1H-indol-2-yl]-morpholin-4-yl-methanone,
and pharmaceutically acceptable salts thereof 8. A process for the manufacture of a compound according to claim 1, comprising the steps of
a) reacting the compound of the formula II

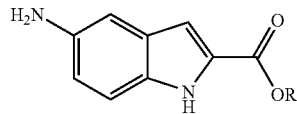

II wherein R is lower alkyl, with a ketone of the formula III

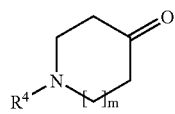

III wherein $R^4$ and m are as defined in claim 1, in the presence of a reducing agent and an acid to obtain a compound of the formula IV

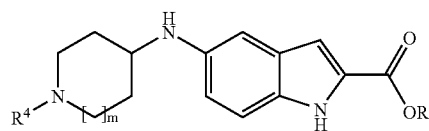

IV and, after saponification of the ester,
b) coupling the compound of formula V

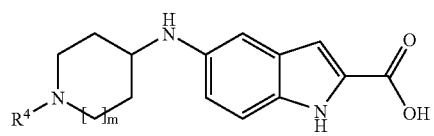

V with an amine of the formula VI

H—NR¹R²    VI wherein $R^1$ and $R^2$ are as defined in claim 1, under basic conditions to obtain a compound of the formula I
and if desired,
converting the compound obtained into a pharmaceutically acceptable acid addition salt.

9. A pharmaceutical composition, comprising a therapeutically effective amount of a compound according to claim 1 and a pharmaceutically acceptable carrier and/or adjuvant.

10. A method for the treatment of diabetes, comprising the step of administering a therapeutically effective amoutn of a compound according to claim 1 to a human being or animal in need thereof.

11. A method for the treatment of obesity in a human being or animal, comprising the step of administering a therapeutically effective amount of a compound of formula 1 according to claim 1 in combination or association with a therapeutically effective amount of other drugs for the treatment of obesity or eating disorders to said human being or animal in need thereof.

* * * * *